United States Patent
Tyrrell et al.

(10) Patent No.: US 6,216,022 B1
(45) Date of Patent: Apr. 10, 2001

(54) IMPLANTABLE OPTICAL MEASUREMENT DEVICE AND METHOD FOR USING SAME

(75) Inventors: Steven P. Tyrrell, Highland Park; Shannon J. Ebner, Chicago, both of IL (US)

(73) Assignee: Biosafe Laboratories, Inc., Chicago, IL (US)

( * ) Notice: Subject to any disclaimer, the term of this patent is extended or adjusted under 35 U.S.C. 154(b) by 0 days.

(21) Appl. No.: 09/599,139

(22) Filed: Jun. 22, 2000

(51) Int. Cl.[7] .................................................. H61B 5/00
(52) U.S. Cl. ............................................. 600/310; 600/316
(58) Field of Search .................................... 600/310, 316, 600/322, 323, 326, 327, 339, 341, 342, 473, 476

(56) References Cited

U.S. PATENT DOCUMENTS

| 4,704,029 | 11/1987 | Van Huuvelen . |
| 4,803,992 | * 2/1989 | Lemelson ............................. 600/342 |
| 5,127,406 | 7/1992 | Yamaguchi . |
| 5,222,495 | 6/1993 | Clarke et al. . |
| 5,277,181 | 1/1994 | Mendelson et al. . |
| 5,368,028 | 11/1994 | Palti . |
| 5,598,841 | * 2/1997 | Taniji et al. ......................... 600/342 |
| 5,605,152 | 2/1997 | Slate et al. . |
| 5,628,310 | 5/1997 | Rao et al. . |
| 5,823,951 | 10/1998 | Messerschmidt . |
| 6,002,954 | * 12/1999 | Van Antwerp et al. ............. 600/310 |
| 6,049,727 | * 4/2000 | Crothall .............................. 600/310 |

* cited by examiner

*Primary Examiner*—Eric F. Winakur
(74) *Attorney, Agent, or Firm*—Brinks Hofer Gilson & Lione

(57) ABSTRACT

A method and apparatus for making an optical measurement through a tissue such as skin of a person includes an implantable optical system having an entry window, an exit window, a reference path between the windows and a measurement path between the windows. The reference path includes a reference element with known optical characteristics, and the measurement path is in fluid communication with the body fluids of the person. A first optical signal is directed through the tissue of the person, the entry window, the reference path, the exit window and the tissue of the person to an external optical sensor, and a second optical signal is directed through the same portion of the tissue of the person, the entry window, the measurement path, the exit window and the same portion of the tissue of the person to the external optical sensor. Variations in the optical effects of the tissue on the measurement can be measured with the second optical signal and used to improve measurement accuracy. A blocking element fills a measurement region in the measurement path when measurements are not being made. This blocking element prevents the accumulation of tissue in the measurement region.

20 Claims, 7 Drawing Sheets

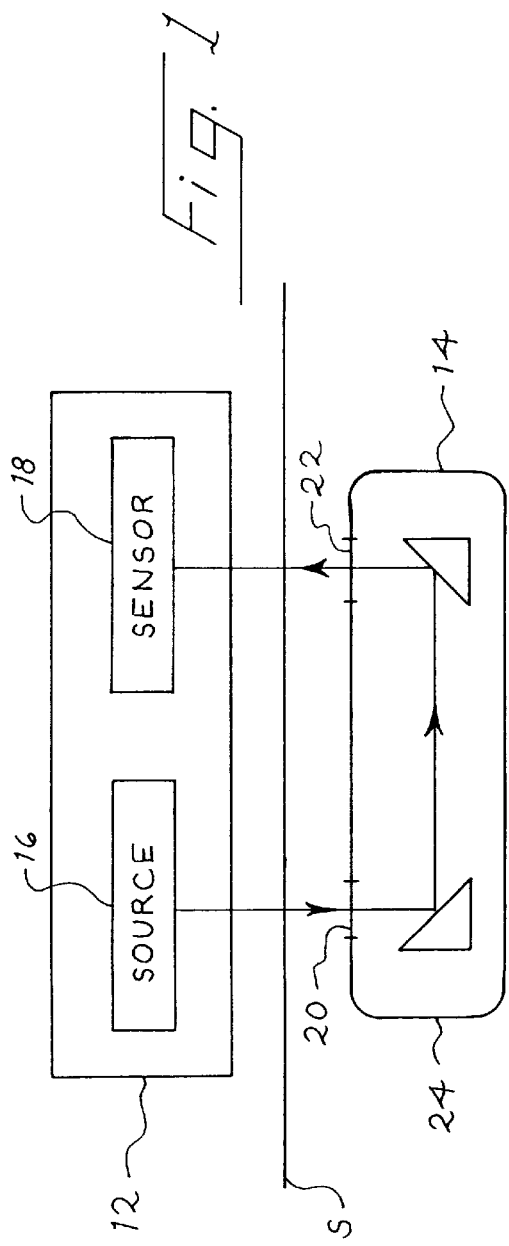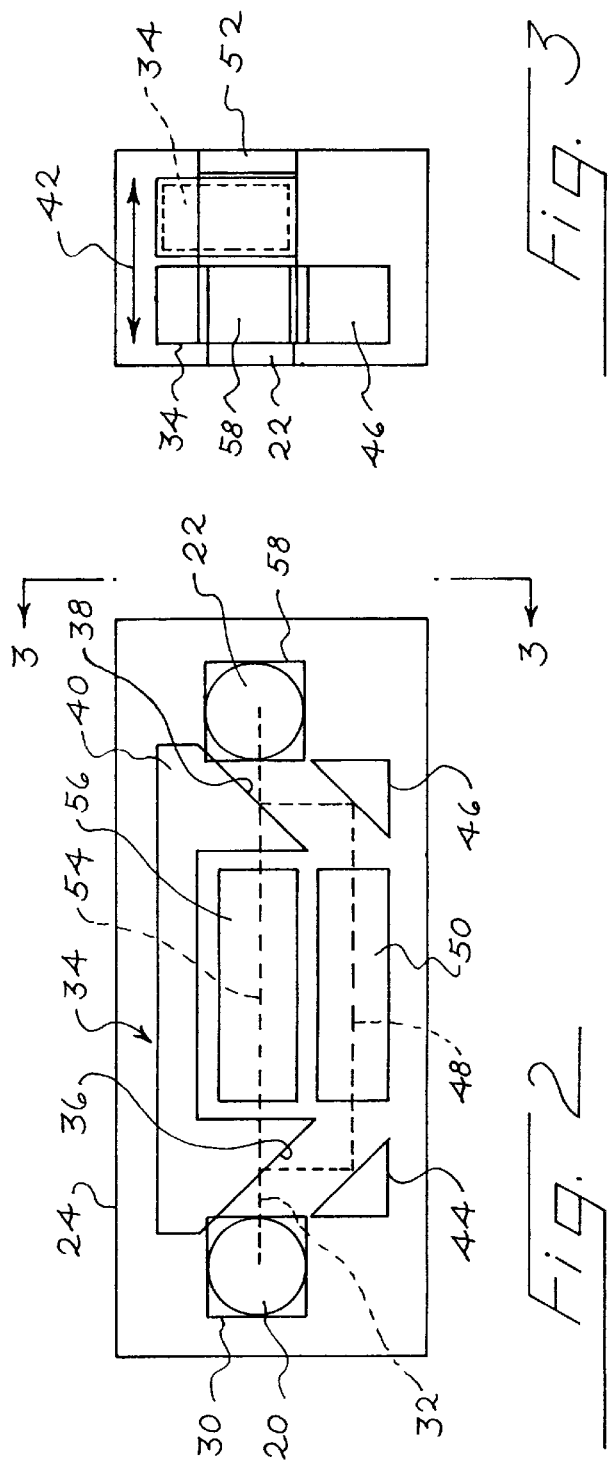

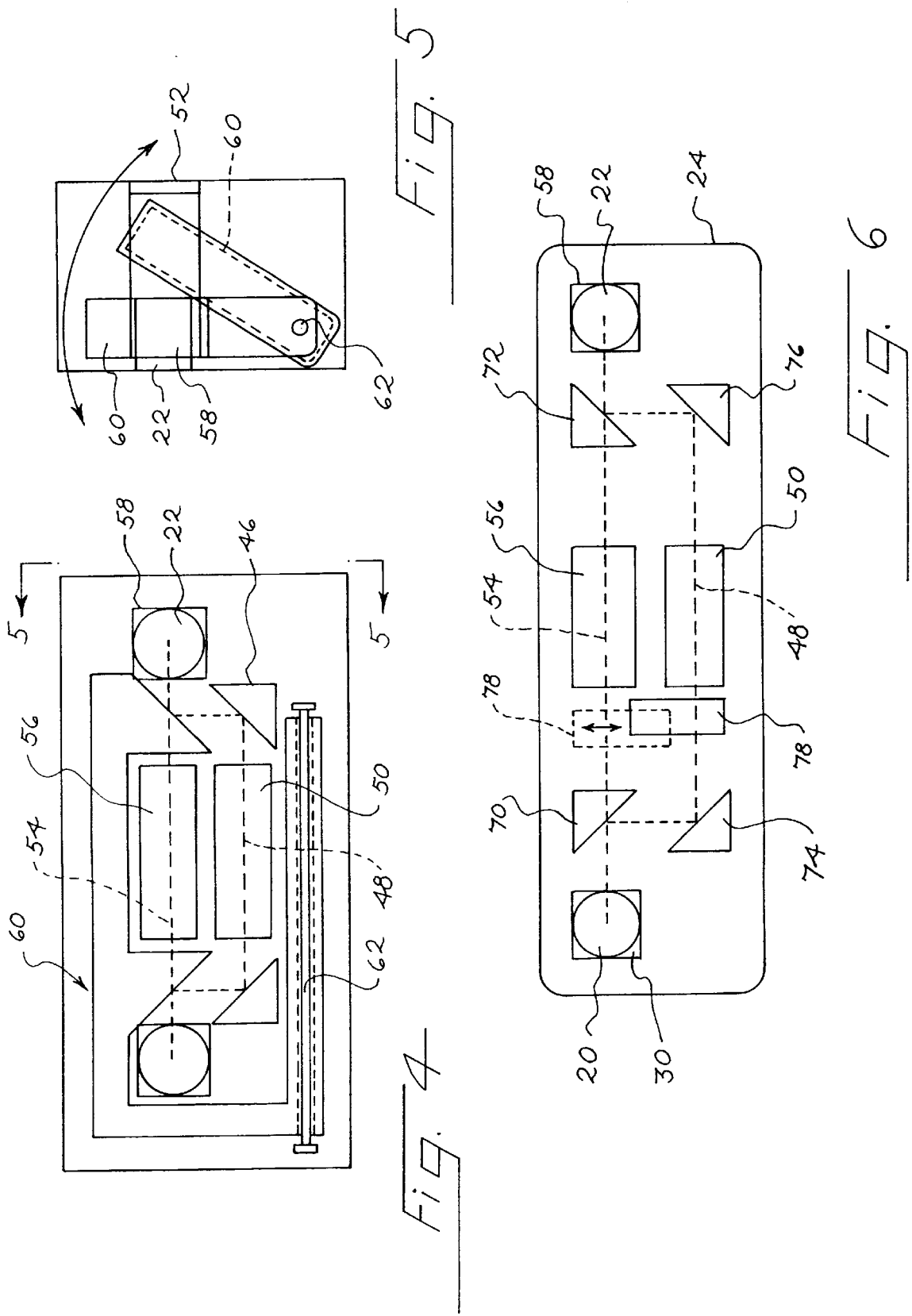

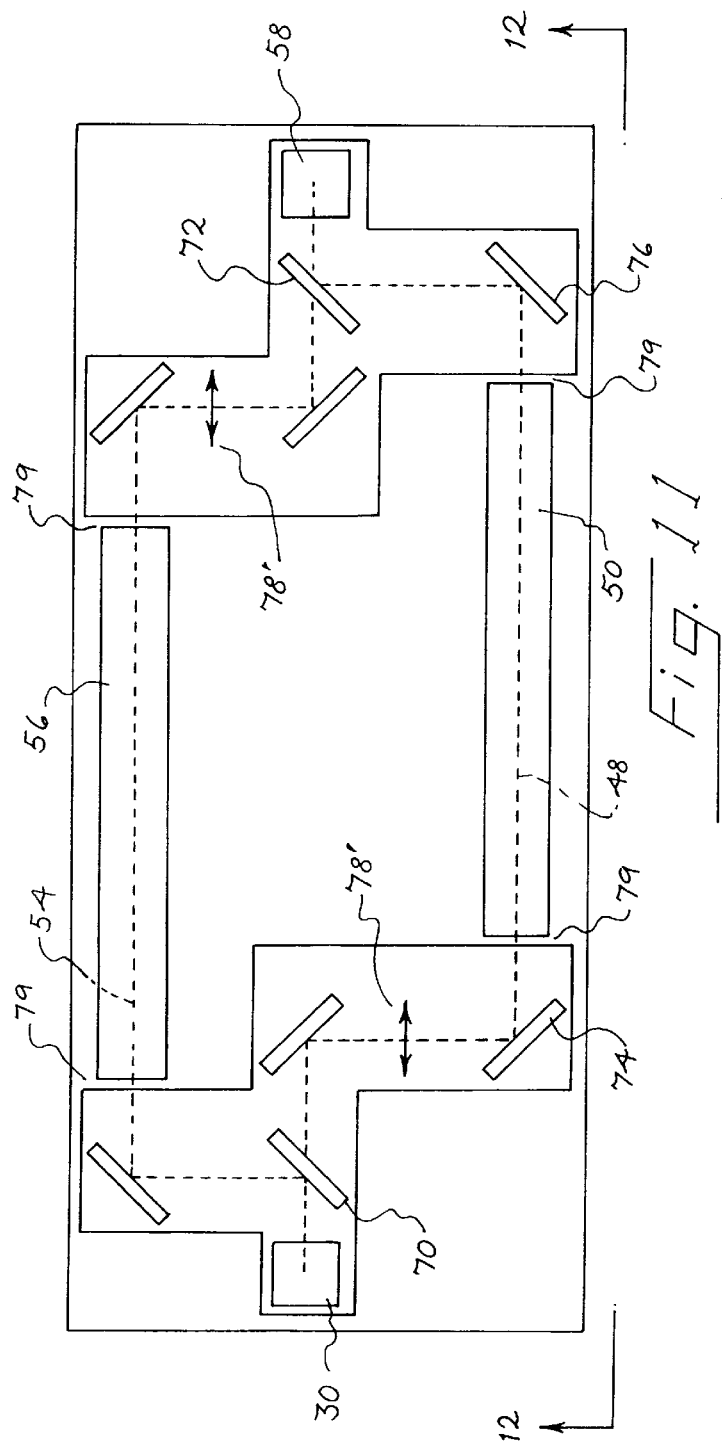
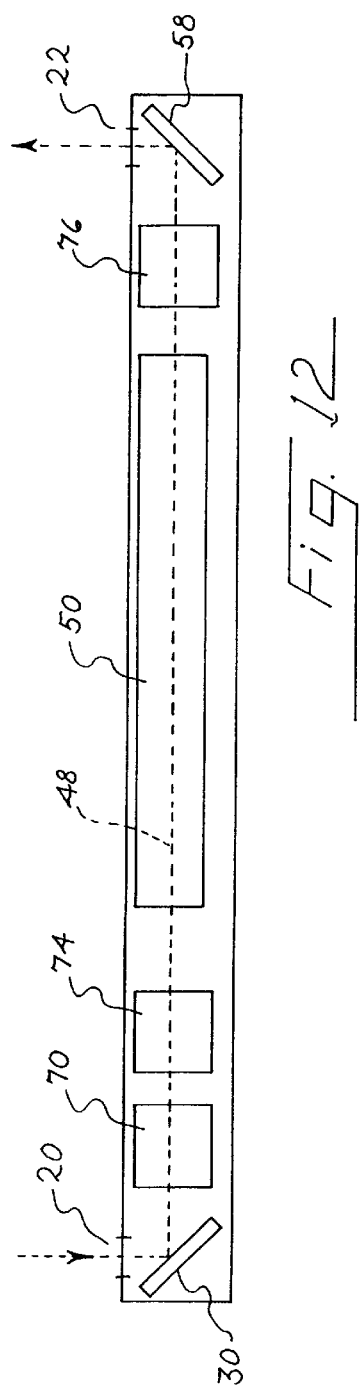

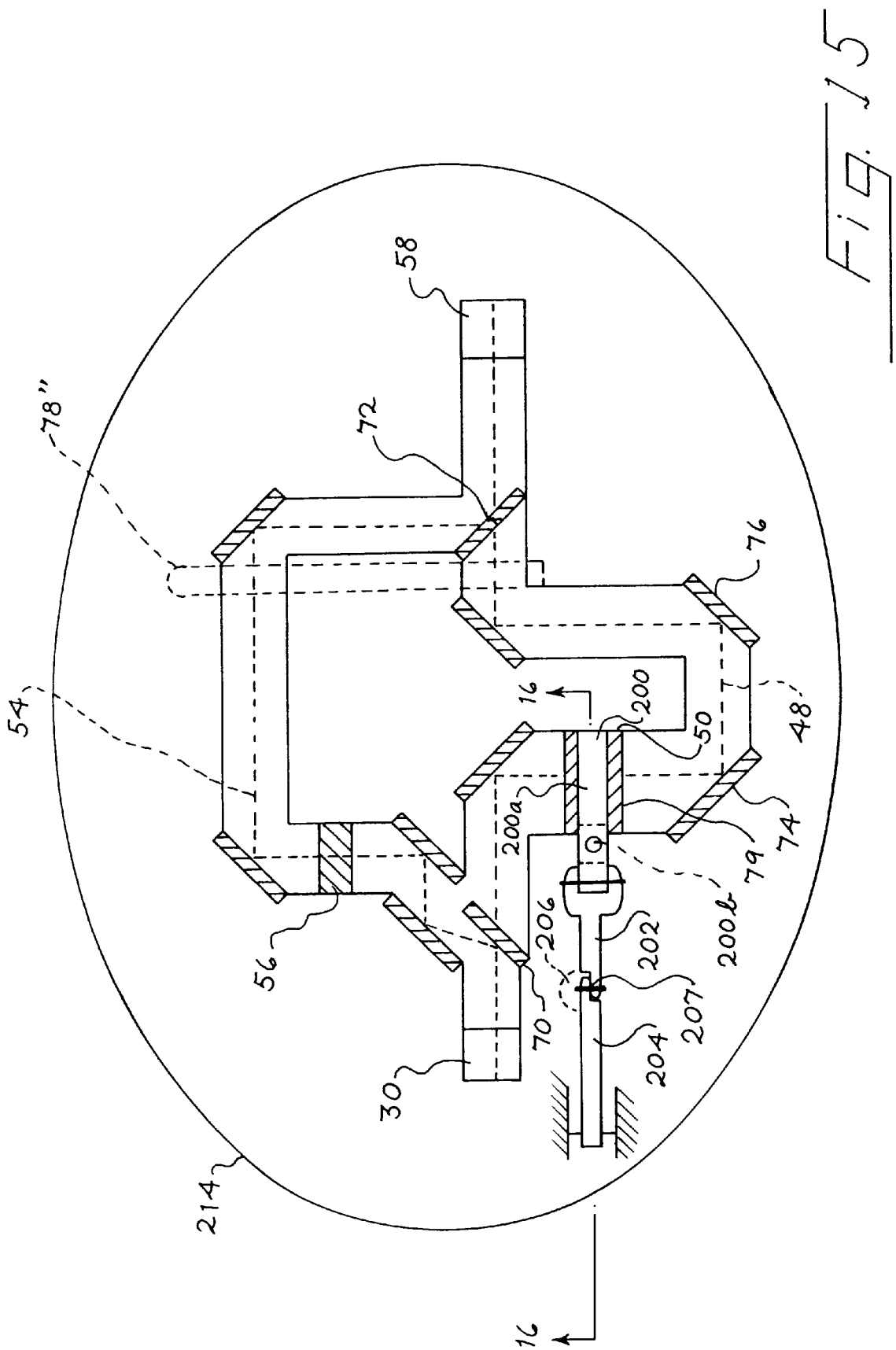

IMPLANTABLE OPTICAL MEASUREMENT DEVICE AND METHOD FOR USING SAME

BACKGROUND

The present invention relates to systems for optically measuring biological parameters, such as glucose concentration for example.

There has been substantial activity in the field of optical measurement of biological analytes. One approach is to make such measurements using noninvasive optical systems that direct an optical signal against the skin of a person and measure optical characteristics of reflected, transmitted or scattered light. Messerschmidt U.S. Pat. No. 5,823,951, Mendelson U.S. Pat. No. 5,277,181, Clarke U.S. Pat. No. 5,222,495, and Yamaguchi U.S. Pat. No. 5,127,406 are examples of such noninvasive measurement systems. A recurring problem with this approach is that the skin of the person absorbs, scatters and otherwise affects optical signals to a substantial degree, thereby interfering with the desired measurement. Interference of this type can vary substantially from person to person, and such variations can make it difficult or impossible to achieve high accuracy noninvasive optical measurements.

In principle, it would be possible to implant an entire optical measuring system, thereby eliminating adverse effects of the skin on the optical measurement. See Van Heuvelen U.S. Pat. No. 4,704,029. However, such an implantable system would require power for operation which would represent yet another disadvantage.

Various approaches have been suggested for combining an external optical source and sensor with an implantable optical system. See, for example, Rao U.S. Pat. No. 5,628,310, Palti U.S. Pat. No. 5,368,028, and Slate U.S. Pat. No. 5,605,152. The system described in the Slate patent overcomes the problem of skin interference by using a fiber optic cable to interconnect the internal and external portions of the system. The devices disclosed in the Rau and Palti patents suffer from the disadvantage that variations in the optical characteristics of the skin can adversely effect the optical measurement.

Thus, a need presently exists for an improved implantable optical system that reduces or eliminates measurement problems associated with variations in the optical characteristics of the skin.

SUMMARY

The preferred embodiments described below provide an implantable optical system intended to be placed under a tissue such as the skin of a person. This optical system includes an entry window, an exit window, and a measurement path between the windows. The measurement path traverses a measurement region that is open to body fluids. A blocking element is normally positioned in the measurement region to prevent tissue from entering the measurement region. This blocking element is temporarily removed from the measurement region to allow a measurement to be made, and then the blocking element is replaced.

Preferably, the optical system also includes a reference path. The reference path includes a reference element that provides a predetermined optical characteristic. In use, a first optical signal is directed through the tissue of the person, the entry window, the reference path, the exit window, and the tissue to an optical sensor. Then a second optical signal is directed through the tissue, the entry window, the measurement path, the exit window, and the tissue to the optical sensor. The first and second optical signals pass through the same portion of the tissue, and thus the first optical signal can be used to compensate for absorption, scattering and other optical effects of the tissue on the second optical signal.

The foregoing paragraphs have been provided by way of introduction, and they are not intended to limit the scope of the following claims.

BRIEF DESCRIPTION OF THE DRAWINGS

FIG. 1 is a schematic diagram of an optical sensing system including an implantable optical system.

FIG. 2 is a top view of a first embodiment of the implantable optical system of FIG. 1.

FIG. 3 is an end view taken along line 3—3 of FIG. 2.

FIG. 4 is a top view of a second embodiment of the implantable optical system of FIG. 1.

FIG. 5 is an end view taken along line 5—5 of FIG. 4.

FIGS. 6, 7 and 8 are top views of alternative embodiments of the implantable optical system of FIG. 1.

FIG. 11 is a top view of another embodiment of the implantable optical system of FIG. 1.

FIG. 12 is a side view taken along line 12—12 of FIG. 11.

FIG. 15 is a top view of an embodiment of the optical system of FIG. 1 that includes a blocking element for the measurement region.

DETAILED DESCRIPTION OF THE PRESENTLY PREFERRED EMBODIMENTS

Figure 7:
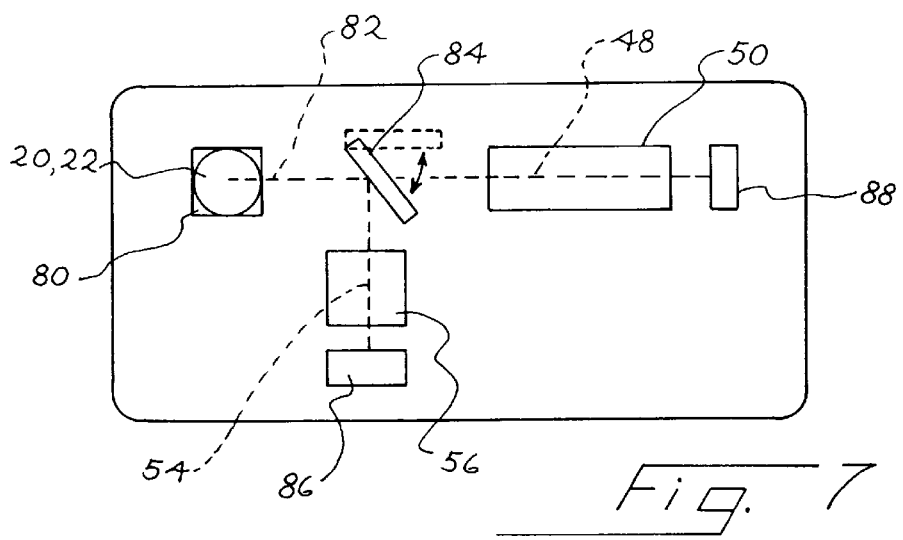

Turning now to the drawings, FIG. 1 shows a block diagram of an optical system 10 that includes a sensor system 12 and an implantable optical system 14. The surface of the skin of the person is schematically indicated at S.

The sensor system 12 includes an optical source 16 and an optical sensor 18. The source 16 directs an optical signal having desired spectral characteristics through the skin S to the implantable optical system 14. The implantable optical system 14 (which will be described in various embodiments below) selectively passes the incoming optical signal through either a measurement path or a reference path before returning the optical signal through the skin S to the sensor 18. The implantable optical system 14 includes a biocompatible housing 24, and an entry window 20 and an exit window 22 mounted in the housing 24. Optical signals from the source 16 pass through the entry window 20, whether destined for the measurement path or the reference path. Similarly, optical signals from both the reference path and the measurement path pass via the exit window 22 to the sensor 18. Thus, reference path signals and measurement path signals pass through precisely the same portions of the skin S. The reference path signals can be used to normalize the measurement path signals to substantially eliminate inaccuracies due to variations in the optical characteristics of the skin from person to person.

FIGS. 2 and 3 provide top and end views of a first embodiment of the implantable optical system 14. FIG. 2 shows the entry window 20, the exit window 22 and the housing 24 described above. Immediately beneath the entry window 20 is a 45° mirror 30 that reflects the incoming optical beam from an initial path perpendicular to the plane of FIG. 2 to the path 32. The 45° mirror 30 is fixed in place to the housing 24. An optical signal reflected by the 45° mirror 30 traverses one of two paths within the housing 24, depending upon the position of an optical switch 34. The optical switch 34 includes two 45° mirrors 36, 38 that are interconnected by a bar 40. The optical switch 34 is movable between a reference and measurement position along the direction 42 shown in FIG. 3. When the optical switch 34 is in the measurement position, the mirrors 36, 38 cooperate with fixed 45° mirrors 44, 46 to direct the optical signal through a measurement path 48. This measurement path passes through a region 50 that is in fluid communication with the external environment of the body adjacent to the housing 24. The housing includes a port 52 that admits biological fluids into the region 50 and the measurement path 48. For example, the region 50 may be filled with a porous plastic or foam that allows biological fluids to enter the region 50, but that substantially retards or prevents the ingress of solid tissues. If such a foam is used, it should preferably be selected to be nonabsorbing in the optical frequency band of interest.

When the optical switch 34 is moved to the reference position by sliding it downwardly, away from the windows 20, 22 along the direction 42, the mirrors 36, 38 are moved out of the path 32, and an optical signal from the mirror 30 passes along a reference path 54 through a reference cell 56. The reference cell 56 includes a material that provides a known optical interaction with the optical signal. For example, the reference cell 56 can be filled with a fluid that absorbs the optical signal to a degree comparable to the absorption of a known concentration of glucose.

Light from the measurement path 48 or the reference path 54 (depending upon the position of the optical switch 34) strikes a fixed 45° mirror 58 and is reflected upwardly through the exit window 22.

The position of the optical switch 34 is preferably controlled remotely. For example, the optical switch 34 can include a ferromagnetic material in the bar 40. An external magnet in the sensor system of FIG. 1 can be used to pull the optical switch 34 to the measurement position, and a spring (not shown) can be used to bias the optical switch 34 to the reference position in the absence of an adequate magnetic force holding it in the measurement position. Alternately, a magnet can be included in the optical switch 34 and an external magnet (not shown) in the sensor system can be used to move the optical switch 34 to the measurement position or to the reference position as desired. The presence, absence and polarity of a magnetic signal supplied by the sensor system can be taken as examples of control signals used to control the position of the optical switch 34. The advantage of this approach is that the implantable optical system 14 is entirely passive and requires no internal power source.

FIGS. 4 and 5 are schematic views of a second preferred embodiment of the implantable optical system 14 of FIG. 1. The embodiment of FIGS. 4 and 5 is similar to the embodiment of FIGS. 2 and 3, and the same reference symbols are used for comparable elements. The principal difference is that the embodiment of FIGS. 4 and 5 uses an optical switch 60 that is pivotably mounted to hinge about a hinge axis 62. The optical switch 60 can be pivoted, for example using magnetic forces as described above, between a reference position shown in dotted lines in FIG. 5 (in which the optical signal passes through the reference cell 56) and a measurement position shown in solid lines in FIG. 5 (in which the optical signal passes through the measurement region 50).

The optical switch used in certain embodiments of this invention is not intended to be limited to any particular arrangement. Those skilled in the art will recognize that many optical switches can be adapted for use with this invention, and the term "optical switch" is intended broadly to encompass any system for directing an optical signal selectively to one of at least two optical paths, e.g. by reflecting, blocking, focusing, filtering or otherwise.

FIG. 6 shows another embodiment of the implantable optical system 14 of FIG. 1. In the system of FIG. 6, an optical signal from the mirror 30 is directed against a beam splitter 70 that divides the incoming beam into two partial beams. The first partial beam is directed along a reference path 54 through the reference cell 56, a second beam splitter 72 to the mirror 58 and the exit window 22. The second partial beam from the beam splitter 70 is deflected by a fixed mirror 74 along a measurement path 48 through the measurement region 50 to another fixed mirror 76, the beam splitter 72, the mirror 58 and the exit window 22.

In this embodiment, the optical switch takes the form of a movable shutter 78 that can be moved between a reference position (as shown as solid lines in FIG. 6) and a measurement position (as shown in dotted lines in FIG. 6). In the reference position, the shutter 78 blocks the passage of light along the measurement path 48, and the only light that emerges from the exit window 22 is that which has passed along the reference path 54 through the reference cell 56. Conversely, when the shutter 78 is moved to the dotted line position of FIG. 6, the shutter 78 blocks the passage of light through the reference cell 56. In this case, all of the light emerging from the exit window 22 has passed along the measurement path 48 through the measurement region 50.

FIGS. 11 and 12 show another embodiment of the implantable optical system 14 of FIG. 1. The embodiment of FIGS. 11 and 12 is similar to that of FIG. 6, and the same reference numerals are used for comparable elements. The embodiment of FIGS. 11 and 12 differs somewhat in the optical layout, and two shutters 78" are substituted for the single shutter 78 of FIG. 6. Also, the optical elements are encapsulated in separate housings and provided with appropriate windows 79. The embodiment of FIGS. 11 and 12 operates quite similarly to the embodiment of FIG. 6 described above.

Yet another embodiment of the implantable optical system 14 of FIG. 1 uses a movable mirror to select either the reference path or the measurement path. As shown in FIG. 7, in this embodiment the entry and exit windows 20, 22 are aligned with one another, and they can in fact correspond to the same physical element. Light entering the system via the entry window 20 is deflected by a fixed 45° angle mirror 80 along a path 82 toward an optical switch 84. The optical switch in this embodiment is a mirror which can be moved between first and second positions. In the first position shown in solid lines in FIG. 7, the mirror 84 deflects the optical beam along a reference path 54 through a reference cell 56 to a mirror 86. The mirror 86 returns the optical signal along the reference path 54, the mirror 84 and the mirror 80 to the exit window 22.

When the optical switch is moved to the dotted line position of FIG. 7, the optical beam along the path 82 does not interact with the mirror 84, but instead passes along a measurement path 48 through a measurement region 50 to a mirror 88. The mirror 88 is oriented to return the reflected beam along the same measurement path 48 to the mirror 80 and out the exit window 22.

Figure 13:
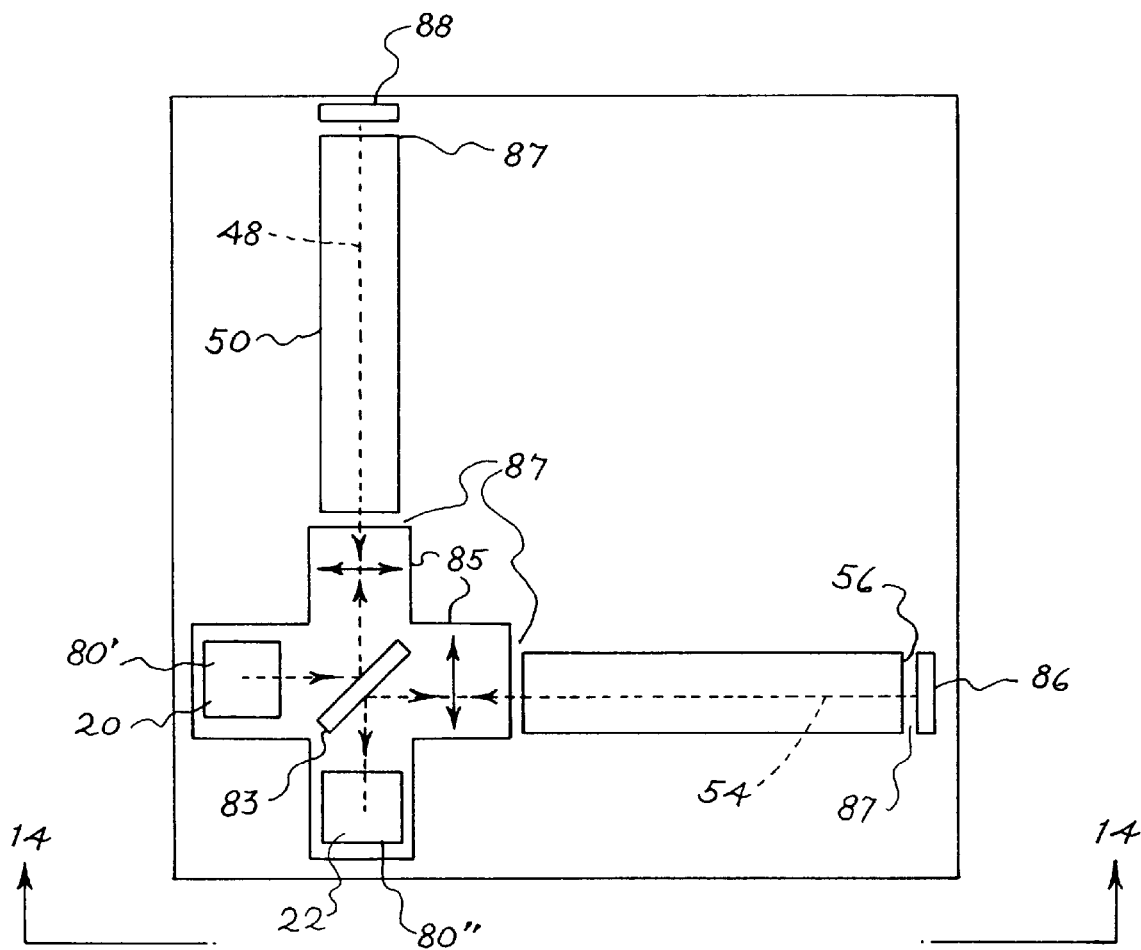
FIG. 13 is a top view of yet another embodiment of the implantable optical system of FIG. 1.
Figure 14:
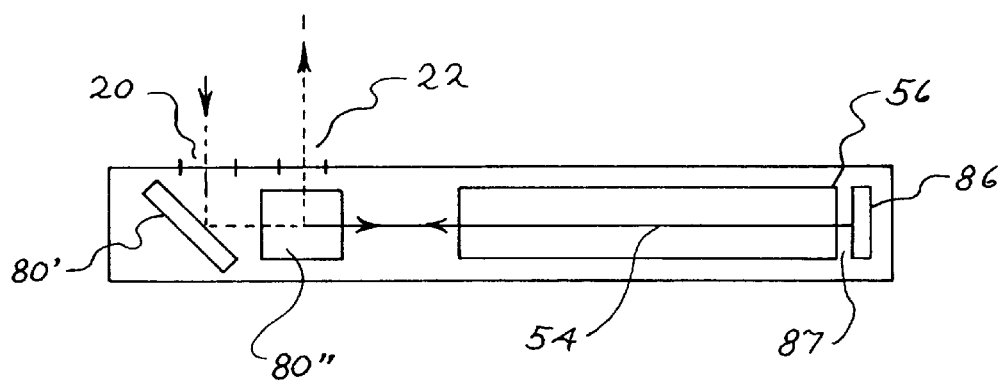
FIG. 14 is a side view taken along line 14—14 of FIG. 13.

FIGS. 13 and 14 relate to another embodiment of the implantable optical system 14 of FIG. 1 that is quite similar to the embodiment of FIG. 7 described above. The principal differences are that the entrance and exit windows are spatially separated and separate fixed 45° mirrors 80N, 80O are used instead of the single mirror 80N of FIG. 7. Also, a shutter 85, which can use either a single or multiple movable elements, is substituted for the movable mirror 84 of FIG. 7. Also, the optical elements are enclosed in a housing provided with appropriate windows 87. In FIG. 13 the element 83 is a beam splitter.

Figure 8:
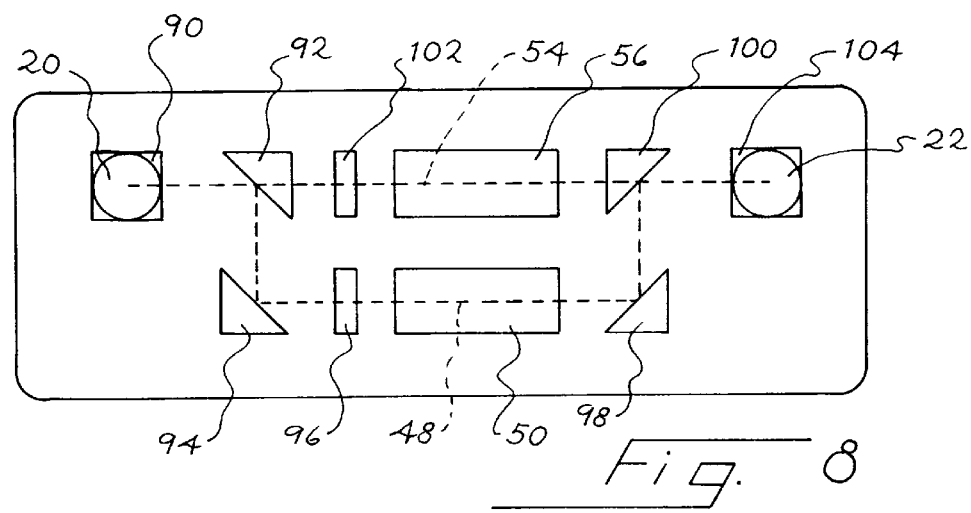

FIG. 8 shows yet another embodiment of the implantable optical system 14 of FIG. 1. In this embodiment, an incoming light beam is selectively directed along a reference path 54 through a reference cell 56 or along a measurement path 48 through a measurement region 50 without the use of any movable optical switch. In the embodiment of FIG. 8, incoming light entering the implantable optical system via the entry window 20 is deflected by a fixed 45° mirror 90 against a beam splitter 92 that divides the incoming beam into two partial beams. The first partial beam is deflected by the beam splitter 92 and a fixed 45° mirror 94 through a polarizer 96 to the measurement region 50. Light emerging from the measurement region 50 is deflected by a fixed 45° mirror 98 to a beam splitter 100, and by the beam splitter 100 to a fixed 45° mirror 104 and the exit window 22. The second partial beam is passed by the beam splitter 92 through a second polarizer 102 to a reference path 54 that passes through a reference cell 56, and then via the beam splitter 100 to the 45° mirror 104 and out via the exit window 22.

All of the optical components shown in FIG. 8 are fixed, but the polarizers 96, 102 are arranged to have differing polarization characteristics. The embodiment of FIG. 8 is intended for use with an optical system that can provide incoming light to the entry window 20 of two differing polarization characteristics. Incoming light of the first polarization characteristic is passed by the first polarizer 96 and blocked by the second polarizer 102, while incoming light of the second polarization characteristic is blocked by the polarizer 96 and passed by the polarizer 92. For example, the polarizers 96, 102 can be characterized by polarization directions that differ by 90°. Alternately, the polarizers 96, 102 can be right and left circular polarizers. By properly choosing the polarization characteristic of the light emitted by the source 16 of FIG. 1, light can be selectively directed along either the measurement path 48 or the reference path 54, or light can be simultaneously directed along both paths 48, 54. The sensor preferably includes one or more polarizers to distinguish the beams from the two paths if the beams are simultaneous in time.

Variable opacity elements used in optical switches can be controlled using optical, magnetic, electrical, or thermal control signals. When movable reflectors are used in an optical switch, the movable reflectors can be mounted to vibrate, rotate, hinge, pivot, or slide, and the forces used to move the movable reflector can be generated magnetically, electrically or using mechanical pressure.

As pointed out above, optical switches can use variable opacity elements, such as spectral filters or polarization filters for example. Spectral filters can be formed as interference filters, and they can be positioned to direct an incoming optical beam of a selected spectral distribution into a selected one of the reference and measurement paths.

As yet another alternative, the reference cell or reference element may be mounted to move into and out of the measurement path. The incremental absorption provided by the reference cell can then be used to calibrate the measurement. Such a movable reference cell can be mounted to translate, rotate or pivot using magnetic, electric or mechanical pressure to achieve the desired movement. In this alternative, the term "measurement path" should be interpreted as the path of the optical beam when the reference cell is out of alignment with the measurement region such that the optical beam passes through the measurement region but not the reference cell. The term "reference path" should be interpreted as the path through which the optical beam passes when the reference cell is aligned with the measurement region such that the optical beam passes through both the reference cell and the measurement region.

The foregoing examples have provided a single reference path and a single measurement path. Of course, it should be understood that two or more reference paths and two or more measurement paths can be provided in a single implantable optical system.

The foregoing examples have been discussed in the context of an external sensor system that is positioned outside the body of the person. In this case, the optical signals passing between the sensor system and the implantable optical system traverse the skin and optionally other tissues such as bone, blood, fat, vessel wall and muscle. For example, the implantable optical system may be placed within the skull or within the abdominal cavity. In other embodiments, the sensor system may be positioned within the body of the person. In this case, the optical signals will traverse other tissues such as bone, blood, fat, muscle and vessel wall, without traversing the skin.

Figure 9:
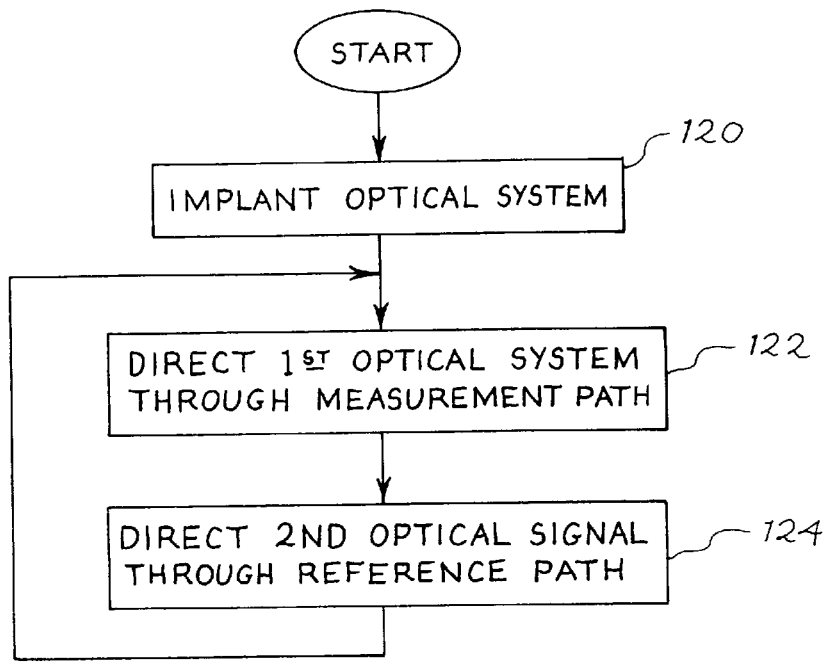
FIG. 9 is a flow chart of a method for using the optical system of FIG. 1.

FIG. 9 provides a flow chart of a method that can be implemented with the system 10 of FIG. 1. At block 120, an optical system is implantable into a person. Any of the implantable optical systems described above can be used. At block 122 a first optical signal is passed through the measurement path (but not the reference path) of the implantable optical system. This first optical signal is used to obtain an optical measurement of a desired biological parameter such as blood glucose concentration.

At block 124, a second optical signal is directed through the reference path of the implantable optical system. The second optical signal is used to obtain a measurement of the known reference cell or reference element. As explained above, the first and second optical signals of blocks 122 and 124 pass through the same tissues of the person being monitored, and thus the optical effects of passage through the tissues can be accounted for in the second optical signal through the reference path and then used to calibrate the first optical signal passing through the measurement path. As shown in FIG. 9, the first and second optical signals can be repeatedly directed through the respective paths. As discussed above, the first and second optical signals can be sequential (in either order) or simultaneous in time.

In one preferred embodiment the method of FIG. 9 is repeated many times such that multiple first optical signals and multiple second optical signals are passed through the implantable optical system. Preferably, the first optical signals are interleaved with the second optical signals. When the first optical signals are averaged and the second optical signals are averaged, errors due to tissue movement such as blood flow are reduced even further.

Many of the advantages of the present invention are achieved when the first and second optical signals pass through substantially though not precisely the same tissues. As used herein the optical signals are said to pass through substantially the same tissues if the second optical signal can be used to reduce person-to-person variation in the first optical signal or otherwise to improve the accuracy of a measurement of a biological analyte.

Figure 10:
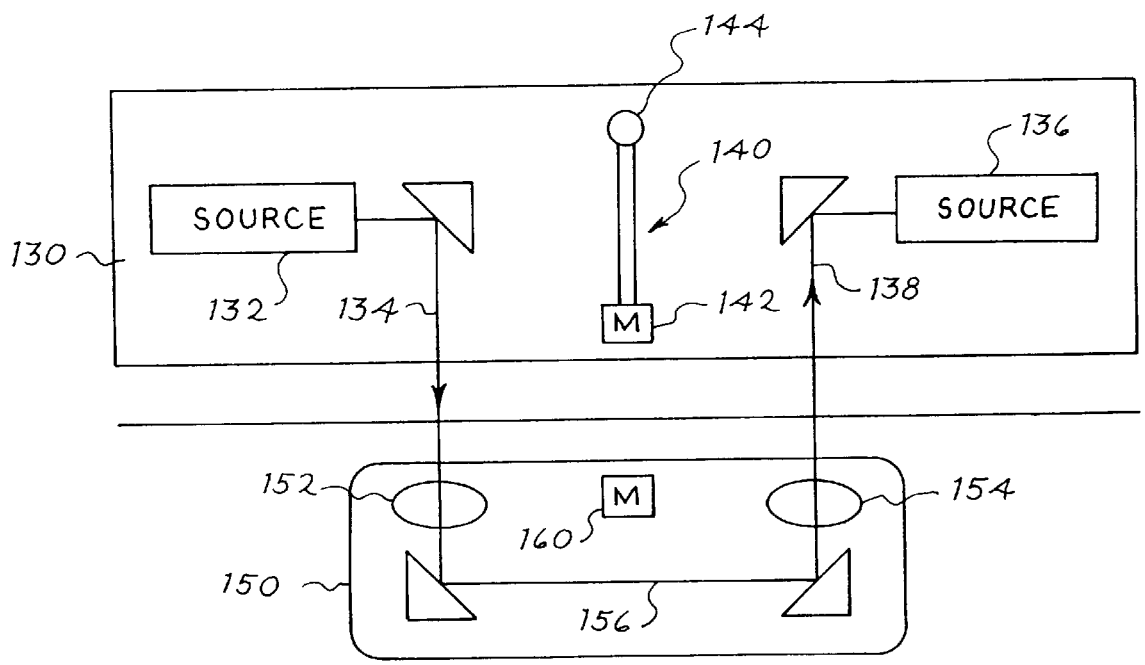
FIG. 10 is a block diagram of an optical measuring system including a magnetic locating system.

Proper alignment between the sensor system 12 and the implantable optical system 14 of FIG. 1 improves the accuracy and reliability of the measurement. FIG. 10 schematically illustrates a preferred system for achieving the desired alignment. The system shown in FIG. 10 includes an external optical system 130 that includes an optical source 132 that directs an optical beam along the optical axis 134 and an optical sensor 136 that responds to incoming optical radiation along the optical axis 138. The external sensor system 130 also includes a magnetic locator 140 that in this embodiment includes a magnet 142 suspended on a tension member such as a rod or a filament so as to pivot about a mounting point 144.

The system of FIG. 10 also includes an implantable optical system 150 that includes an entry window 152 and means for directing incoming radiation from the entry window 152 along a measurement path 156 to an exit window 154. The implantable optical system 150 includes a second magnet 160. As before, the reference symbol S is used to represent the skin of the person under which the implantable optical system 150 is implantable. The implantable optical system 150 may include a reference path as described above, or alternately it may not.

Proper alignment between the external sensor system 130 and the implantable optical system 150 is achieved when the optical axes 134, 138 are aligned with the windows 152, 154, respectively. This state of alignment can be achieved by using the magnetic locator 140 to locate the magnet 160. The magnet 160 is positioned such that the when the magnet 160 is directly under the magnet 142, the windows 152,154 are aligned with the optical axes 134, 138, respectively. If desired, two magnetic locators can be used to provide guidance regarding orientation.

Many alternatives are possible to the system of FIG. 10. For example, the magnet 142 can be replaced with a non-magnetic ferromagnetic element. Alternately, the magnet 160 can be replaced with a non-magnetic ferromagnetic element. As used herein, the term "ferromagnetic element" is intended broadly to encompass both magnetic and non-magnetic materials that magnetically interact with a magnet. The system of FIG. 10 can also be implemented in an embodiment in which the optical axes 134, 138 are coincident and the windows 152, 154 are coincident. In such an alternative, the magnet 160 is preferably disposed under the windows 152, 154 and the magnetic locator 140 is preferably aligned with the optical axes 134, 138.

Systems That Actively Block Tissue Growth In The Measurement Region

In all of the embodiments described above, the measurement region is in long-term communication with body fluids. In some applications, it is preferred to take active steps to preventing the accumulation of tissue into the measurement region, as in the system of FIGS. 15 and 16. This system is most closely related to that of FIGS. 11 and 12, and comparable components are designated with the same reference symbols.

The implantable optical system of FIG. 15 divides an incoming optical beam that enters through the entry window above the mirror 30 into first and second beams. The first beam passes along a measurement path 48 through a measurement region 50, and the second beam passes along a reference path 54 through a reference cell 56. These two paths are combined at a beam splitter 72, and are then deflected by a mirror 58 out the exit window (not shown). As before, the measurement region 50 is in fluid communication with body fluids, and a shutter 78" is used to block one of the two paths 48, 54, selectively. For example, the shutter 78" can be guided for movement perpendicular to the plane of FIG. 15 between a first position, in which the measurement path 48 is unobstructed and the reference path 54 is obstructed, and a second position, in which the measurement path 48 is obstructed and the reference path 54 is unobstructed. The shutter 78" can be moved between these two positions by magnetic forces that pull or push it into one of the two positions, and a biasing spring (not shown) that restores it to the other.

The embodiment of FIG. 15 includes a blocking element 200 that is guided for movement between a first position shown in FIG. 15 and a second position in which the blocking element 200 is positioned to the right of the position shown in FIG. 15.

In the first position, the blocking element 200 substantially completely occupies the measurement region 50, thereby preventing the accumulation of tissue in the measurement region 50. Such tissue, if present, might interfere with the desired optical measurement. The portion of the blocking element 200 that normally fills the measurement region 50 is indicated at 200a in FIG. 16.

Figure 16:
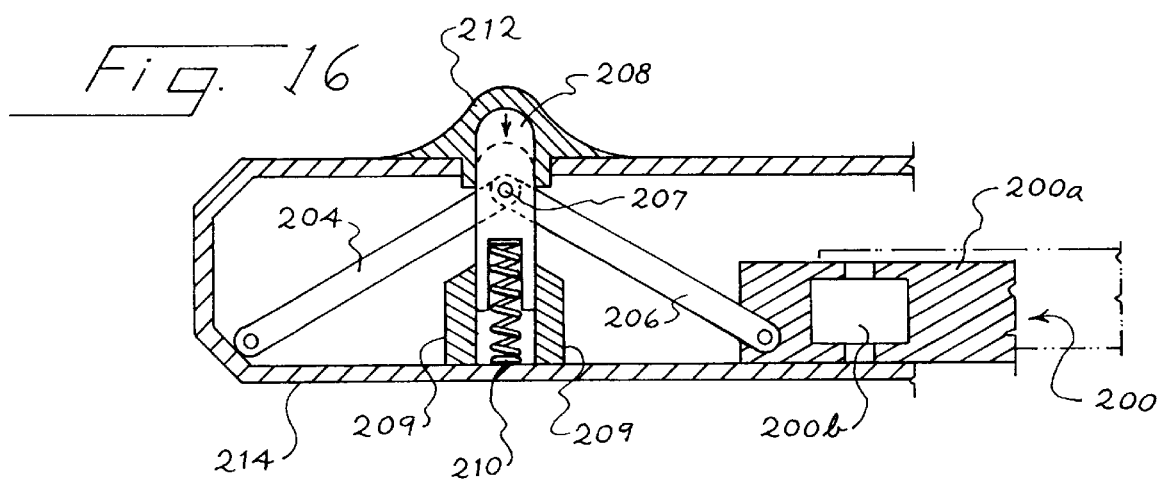
FIG. 16 is a partial sectional view taken along line 16—16 of FIG. 15.

When it is desired to make a body fluid measurement, the blocking element 200 is moved to the right in FIGS. 15 and 16 to bring a second portion 200b of the blocking element 200 into alignment with the measurement path 48. In this second position, the blocking element 200 is disposed outside of the measurement region 50. This allows body fluids to infiltrate the measurement region 50 and the desired measurement to be made.

Many arrangements can be used to selectively position the blocking element 200 as described above. For example, in the embodiment of FIGS. 15 and 16, the blocking element 200 is secured to a linkage including articulated links 204, 206. The links 204, 206 are hinged together at a hinge axis 207, which also connects the links 204, 206 with a slide 208, and the link 204 reacts against the housing 214. The hinge axis 207 and the sliding axis of the blocking element 200 are parallel to the upper surface of the housing 214, and the hinge axis 207 is perpendicular to the sliding axis. The slide 208 is guided for vertical movement in a guide 209, and is biased upwardly in the view of FIG. 16 by a compression spring 210. The uppermost portion of the slide 208 protrudes above the upper surface of the housing 214 through an opening in the housing 214 that is sealed by a resilient cover 212. The rest position of the blocking element 200 is as shown in FIGS. 15 and 16. The biasing force supplied by the spring 210 moves the slide 208 upwardly, and the blocking 200 to the left as shown in the drawings. When it is desired to make a measurement, a sensor (not shown) is physically applied against the skin adjacent the upper surface of the housing 214. This sensor (not shown) depresses the slide 208, thereby moving the blocking element 200 to the right as shown in the drawings in the provided guides. For the duration of the measurement, the open portion 200b of the blocking element 200 is aligned with the measurement region 50, thereby permitting body fluids to infiltrate the measurement region 50 and the desired measurement to be made.

At the conclusion of the measurement, the sensor is removed, and the spring 210 restores the blocking element 200 to the position of FIGS. 15 and 16, in which it prevents the accumulation of tissue in the measurement region 50.

After the optical system has been implanted under the tissue of a person, the spring 210 supplies the biasing force that normally holds the blocking element in the measurement region 50. Pressure on the slider 28 is used to move the blocking element out of the measurement region 50, and an external sensor (not shown) then directs at least one optical signal through the tissue of the person, the entry window (not shown), the measurement path 48, the exit window (not shown) and the tissue of the person to the optical sensor. Once the sensor is removed, the spring 210 automatically repositions the blocking element 200 in the measurement region 50.

The blocking element 200 described above can take many forms, and it can be moved in other ways. For example, external magnetic forces can be used to shift the blocking element 200, and it can be guided for arcuate as opposed to sliding movement. The pressure-receiving element may be coupled with the blocking element indirectly (via intermediate components) or directly. The blocking element 200 suitably modified can be used with any of the embodiments described above. It also may find usage in implantable optical systems that include a measurement path without a reference path of the type described above. By way of example, the housing 214 and the blocking element 200 may be formed of a biocompatible material such as titanium. The cover 212 may be formed of a biocompatible flexible material such as silicone.

Conclusion

It is not intended to limit this invention to any particular type of sensor system. Any suitable optical measuring technique can be used, including those based on infrared absorption spectroscopy, Raman spectroscopy, polarimetry, fluorescence, and attenuated total reflection. Fourier transform infrared spectroscopy is one example of infrared absorption spectroscopy.

Furthermore, this invention is well-suited for use with many different types of biological measurements. For example, this invention can be used to measure blood concentrations of glucose, blood urea nitrogen levels, creatine levels, as well as other biological analytes that can be measured using optical measurement techniques.

The systems described above provide important advantages. Background interference due to tissues such as skin can be substantially eliminated from the measurement, because the measurement signal can be calibrated with the reference signal, and the reference signal is subjected to the same background interference as the measurement signal. In this way, person-to-person variability in the measurement can be substantially reduced. The use of an internal reference cell provides increased accuracy in quantifying the biological parameter being measured. Since the implantable optical system is entirely passive, it requires no power source.

As used herein, the term "window" is intended broadly to encompass any suitable structure for passing an optical signal either into or out of the implantable optical system. Thus, a window can have a lens effect or not, it can be opaque at visible wavelengths or not, and it can be integral with the housing or not, and it can scatter the optical beam to some extent. As pointed out above, the entry and exit windows may be spatially separated or spatially coincident, and in some cases they may be formed by the same physical optical element.

The term "light" is intended broadly to encompass visible, ultraviolet and infrared light. Similarly, the term "optical" is intended broadly to encompass systems or techniques for visible ultraviolet or infrared light.

The term "optical switch" is intended broadly to encompass any device for selectively directing light along one of two or more paths, including optical switches based on movable shutters, movable mirrors (whether metallic or interference-filter type mirrors), lenses, and variable opacity elements whether active or passive.

The term "control signal" is intended broadly to encompass electrical magnetic, optical and other signals that can be used to control the position of an optical switch.

The term "polarization direction" is intended broadly to encompass any polarization direction whether of the type designated by angles (e.g.,0° or 90° polarization) or of the type designed by circular or elliptical polarization direction.

The term "skin" is intended broadly to encompass any body boundary surface, including dermis as well as linings of body cavities, such as the mouth for example.

The term "tissue" is intended broadly to encompass all biological tissues, including by way of example skin, blood, bone, muscle, fat and vessel walls.

The foregoing detailed description has discussed only a few examples of the many ways in which the present invention can be implemented. For this reason, this detailed description is intended by way of illustration, not limitation. It is only the following claims, including all equivalents, that are intended to define the scope of this invention.

What is claimed is:

1. An implantable optical system comprising:
   a biocompatible housing adapted to be inserted under a tissue of a person, said housing comprising an entry window and an exit window, said housing configured to admit biological fluids to a measurement region positioned in an optical path extending between the windows;
   a blocking element mounted in the housing to move between a first position, in which the blocking element substantially occupies the measurement region, and a second position, in which the blocking element is positioned outside the measurement region.

2. The invention of claim 1 further comprising:
   a biasing element biasing the blocking element to the first position;
   a pressure-receiving element movably mounted with respect to at least a portion of the housing, said pressure-receiving element coupled with the blocking element to move the blocking element to the second position in response to applied pressure.

3. The invention of claim 2 wherein the pressure-receiving element comprises first and second links coupled at a hinge axis, said first link reacting against the blocking element, said second link reacting against the housing.

4. The invention of claim 3 wherein the housing comprises an upper surface, wherein the windows are positioned in the upper surface, wherein the blocking element slides along a sliding axis, and wherein the hinge axis and the sliding axis are parallel to the upper surface.

5. The invention of claim 4 wherein the hinge axis is perpendicular to the sliding axis.

6. The invention of claim 1 further comprising:
   a reference element positioned in a second optical path extending between windows; and an optical switch mounted in the housing and operative to direct light through a selected one of the first and second optical paths in response to a control signal.

7. The invention of claim 6 wherein the optical switch comprises a movable reflector.

8. The invention of claim 6 wherein the optical switch comprises a movable shutter.

9. The invention of claim 6 wherein the optical switch comprises a variable opacity element.

10. The invention of claim 1 further comprising:

means for selectively moving the blocking element to the second position.

11. The invention of claim 10 further comprising:

means for biasing the blocking element to the first position.

12. A method for making an optical measurement through a tissue of a person, said method comprising:

(a) implanting an optical system under a tissue of a person, said optical system comprising an entry window, an exit window, a measurement path extending between the windows, and a measurement region in the measurement path, said measurement region accessible to body fluids of the person;

(b) positioning a blocking element in the measurement region;

(c) moving the blocking element out of the measurement region; then (d) directing at least one optical signal through the tissue of the person, the entry window, the measurement path, the exit window, and the tissue of the person, to an optical sensor; and then (e) re-positioning the blocking element in the measurement region.

13. The method of claim 12 wherein acts (b) and (e) position the blocking element to substantially fill the measurement region.

14. The method of claim 12 wherein act (c) comprises applying pressure to the optical system, thereby moving the blocking element out of the measurement region.

15. The method of claim 12 wherein the optical system further comprises a reference optical path between the windows, and wherein the method comprises:

(f) directing another optical signal through the tissue of the person, the entry window, the reference optical path, the exit window, and the skin of the person to the optical sensor.

16. The method of claim 15 wherein act (f) is performed after act (c) and before act (e).

17. The method of claim 15 wherein the optical system implanted in (a) comprises an optical switch operative to direct light through a selected one of the measurement and reference optical paths in response to a control signal.

18. The method of claim 17 wherein act (d) comprises the act of generating the control signal to cause the optical switch to direct light through the measurement optical path.

19. The method of claim 18 wherein act (f) comprises the act of generating the control signal to cause the optical switch to direct light through the reference optical path.

20. The method of claim 15 wherein the optical signals of acts (d) and (f) pass through substantially the same portions of the tissue of the person.

* * * * *